United States Patent [19]
Trojanowski et al.

[11] Patent Number: 5,849,988
[45] Date of Patent: Dec. 15, 1998

[54] RAT COMPRISING STRAIGHT FILAMENTS IN ITS BRAIN

[75] Inventors: John Q. Trojanowski; Virginia M.-Y. Lee, both of Philadelphia, Pa.; Ryong-Woon Shin, Fukuoka, Japan

[73] Assignee: Trustees of the University of Pennsylvania, Philadelphia, Pa.

[21] Appl. No.: 261,810

[22] Filed: Jun. 17, 1994

[51] Int. Cl.$^6$ .............................. C12N 5/00; C12N 15/00; A61K 49/00; A61K 38/00
[52] U.S. Cl. .................. 800/2; 800/DIG. 4; 800/DIG. 5; 435/172.3; 424/9.2; 530/324; 530/352; 530/839
[58] Field of Search .................................. 800/2, DIG. 5, 800/DIG. 4; 435/172.3; 424/9.2; 530/350, 324, 352, 839

[56] References Cited

PUBLICATIONS

Frautschy et al (1991) Proced. Natl. Acad. Sci. 88, 8362–8366.
Podlisny et al (1992) Neurobiol. Aging 13, 561–567, 1992.
Ksiezak–Reading et al (1990) J. Neuro Sci. Res. 25, 420–430, 1990.
Games et al (1992) Neurobiol. Aging 13, 569–576, 1992.
Hardy et al., "Genetic Mistakes Point the Way for Alzeheimer's Disease" The Journal of NIH Research vol. 5: 46–49 (Nov. 1993).
Abraham et al., "Immunochemical Identification of the Serine Protease Inhibitor $\alpha_1$–Antichymotrypsin in the Brain Amyloid Deposits of Alzheimer's Disease," Cell, 52:487–501, 1988.
Arai et al., "Defined Neurofilament, T, and β–amyloid precursor protein epitopes distinquish Alzheimer from non- –Alzheimer senile plaques," Proc. Natl. Acad. Sci. USA, 87:2249–2253, 1990.
Arai et al., "Expression Patterns of β–Amyloid Precursor Protein (β–APP) in Neural and Nonneural Human Tissues from Alzheimer's Disease and Control Subjects," Ann. Neurol., 30:686–693, 1991.
Balin et al., "Neurofilament reassembly in vitro: biochemcal, morphological and immuno–electron microscopic studies employing monoclonal antibodies to defined epitopes," Brain Res., 556:181–195, 1991.
Baudier et al., "Separation of the Different Microtubule–associated Tau Protein Species from Bovine Brain and Their Mode II Phosphorylation by $Ca^{2+}$/Phospholipid–dependent Protein Kinase C," J. Biol. Chem., 262:17584–17590, 1987.
Binder et al., "The Distribution of Tau in the Mammalian Central Nervous System," J. Cell Biol., 101:1371–1378, 1985.
Braak et al., "Occurence of Neuropil Threads in the Senile Human Brain and In Alzheimer's Disease: A Third Location of Paired Helical Filaments Outside of Neurofibrillary Tangles and Neuritic Plaques," Neurosci. Lett., 65:351–355, 1986.

Bramblett et al., "Regions with Abundant Neurofibrillary Pathology in Human Brain Exhibit a Selective Reduction in Levels of Binding–Competent τ and accumulation of Abnormal τ–Isoforms (A68 Proteins)," Lab. Invest.66:212–222, 1992.
Candy et al., "Alumionsilicates and Senile Plaque Formation in Alzheimer's Disease," Lancet, 354–356, 1986.
Candy et al., "Aluminum Accumulation in Relation to Senile Plaque and Neurofibrillary Tangle Formation in the Brains of Patients with Renal Failure", J. Neurol. Sci. 107: 210–218 (1992).
Cole et al., "Ubiquitin–protein conjugates in Alzheimer's lesions," Neurosci. Lett., 79:207–212, 1987.
Garruto et al., "Imaging of calcium and aluminum in neurofibrillary tangle–bearing neurons in parkinsonism–dementia of Guam,"Proc. Natl. Acad. Sci. USA, 81:1875–1879, 1984.
Goedert et al., "The abnormal phosphorylatin of tau protein at Ser–202 in Alzheimer disease recapitulares phosphorylation during development," Proc. Natl. Acad. Sci. USA, 90:5066–5070, 1993.
Goedert et al., "Tau Proteins of Alzheimer Paired Helical Filaments: Abnormal Phosphorylation of All Six Brain Isoforms,"Neuron, 8:159–168, 1992.
Gollin et al., "$\alpha_1$–Antitrypsin and in $\alpha_1$–antichymotrypsin are in the lesions of Alzeheimer's disease," NeuroReport, 3:201–203, 1992.
Good et al., "Selective Accumulation of Aluminum and Iron in the Neurofibrillary Tangles of Alzheimer's Disease: A Laser Microprobe (LAMMA) Study," Ann. Neurol., 31:286–292, 1992.
Greenberg et al., "A preparation of Alzheimer paired helical filaments that displays distinct τ proteins by polyacrylamide gel electrophoresis," Proc. Natl. Acad. Sci. USA, 87:5827–5831, 1990.
Greenberg et al., "Hydrofluoric Acid–treated $\tau_{PHF}$ Proteins Displays the Same Biochemical Properties as Normal τ," J. Biol. Chem., 267:564–569, 1992.
Grundke–Iqbal et al., "Microtubule–associated Protein Tau," J. Biol. Chem., 261:6084–6089, 1986.

(List continued on next page.)

Primary Examiner—Deborah Crouch
Attorney, Agent, or Firm—Law Offices of Jane Massey Licata

[57] ABSTRACT

Methods of generating a rat having Aβ deposits in the brain of the rat by injecting an amount of human A68 protein sufficient to result in formation of the deposits and subsequently examining the rat for the formation of the deposits are disclosed. Rats characterized by the presence of Aβ deposits similar to those found in individuals with Alzheimer's disease are also disclosed. Methods of screening test compositions for prophylactic or therapeutic activity by generating a rat having Aβ deposits in its brain, treating the animal with the test composition and examining the animal for therapeutic or prophylactic effectiveness are also disclosed.

28 Claims, 3 Drawing Sheets

OTHER PUBLICATIONS

Hill et al., "Epitopes Located in Spatially Seperate Domains on Each Neurofilament Subunit Are Present in Parkinson's Disease Lewy Bodies," *J. Comp. Neurol.*, 309:150–160, 1991.

Hyman et al., "Kunitz Protease Inhibitor–Containing Amyloid β Protein Precursor Immunoreactivity in Alzheimer's Disease," *Neuropathol. Exp. Neurol.*, 51:76–83, 1992.

Joachim et al., "Amyloid β–protein deposition in tissues other than brain in Alzheimer's disease," *Nature*, 341:226–230, 1989.

Kidd, "Alzheimer's Disease—An Electron Microscopial Study," *Brain*, 87:307–319, 1964.

Kitamoto et al., "Formic Acid Pretreatment Enhances Immunostaining of Cerebral and Systematic Amyloids," *Lab. Invest.*, 57:230–236, 1987.

Kosik, "Alzheimer's Disease: A Cell Bilogical Perspective," *Science*, 256:780–783, 1992.

Ksiezak–Reding et al., "Mapping of the Alz 50 Epitope in Microtubule–Associated Proteins Tau," *J. Neurosci. Res.*, 25:412–419, 1990.

Lang et al., "Immunological and Conformational Characterization of a Phosphorylated Immunodominant Epitope on the Paired Helical Filaments Found in Alzheimer's Disease," *Biochem. Biophys. Commun.*, 187:783–790, 1992.

Lee et al., "The disordered neuronal cytoskeleton in Alzheimer's disease," *Curr. Opin. Neurobiol.*, 2:653–656, 1992.

Lee et al., "A68: A Major Subunit of Paired Helical Filaments and Derivatized Forms of Normal Tau," *Science*, 251:675–678, 1991.

Lee et al., "Tau Proteins are Abnormally Expressed in Olfactory Epithelium of Alzheimer Patients and Developmentally Regulated in Human Fetal Spinal Cord",.

Mori et al., "Ubiquitin Is a Component of Paired Helical Filaments In Alzheimer's Disease," *Science*, 235:1641–1644, 1987.

Mullan and Crawford, "Genetic and Molecular Advances in Alzheimer's Disease", *Trends Neurosci.* 16: 398–403 1993.

Namba et al., "Apolipoprotein E Immunoreactivity in Cerebral Amyloid Deposits and Neurofibrillary Tangles in Alzheimer's Disease and Kuru Plaque Amyloid in Creutzfeldt–Jakob Disease", *Brain Res.* 541: 163–166 (1991).

Papasozomenos et al., "Phosphorylation Determines Two Distinct Species of Tau in the Central Nervous System," *Cell Motil. Cytoskeleton*, 8:210–226, 1987.

Perl et al., "Alzheimer's Disease: X–ray Spectrometric Evidence of Aluminum Accumulation in Neurofibrillary Tangle–Bearing Neurons," *Science*, 208:297–299, 1980.

Perlmutter et al., "Association Between Vascular Basement Membrane Components and the Lesions of Alzheimer's Disease", *J. Neurosci. Res.* 30: 673–681 (1991).

Perry et al., "Ubiquitin is detected in neurofibrillary tangles and senile plaque neurites of Alzheimer disease brains," *Proc. Natl. Acad. Sci. USA*, 84:3033–3036, 1987.

Perry et al., "Association of Heparan Sulfate Proteoglycan with the Neurofibrillary Tangles of Alzheimer's Disease",*J. Neurosci.* 11: 3679–3683 (1991).

Perry et al., "β Proein Immunoreactivity is Found in The Majority of Neurofibrillary Tangles of Alzheimer's Disease," *Am. J. Pathol.*, 140:283–290, 1992.

Piccardo et al., "Histochemical and X–ray microanalytical localization of aluminum in amyotrophic lateral sclerosis and parkinsonism–dementia of Guam," *ACTA Neuropathol.*, 77:1–4, 1988.

Saunders et al., "Association of apolipoprotein E allele ∈4 with late–onset familial and sporadic Alzheimer's disease," *Neurol.*, 43:1467–1472, 1993.

Schmechel et al., "Increased amyloid β–peptide deposition in cerebral cortex as a consequence of apolipoprotein E genotype in late–onset Alzheimer disease," *Proc. Natl. Acad. Sci. USA*, 90:9649–9653, 1993.

Schmidt et al., "Comparative Epitope Analysis of Neuronal Cytoskeletal Proteins in Alzheimer's Disease Senile Plaque Neurites and Neuropil Threads," *Lab. Invest.*, 64:352–357, 1991.

Selkoe, "Physiological Production of the β–amyloid Protein and the Mechanism of Alzheimer's Disease", *Trends Neurosci.*, 16:403–409, 1993.

Shaw et al., "Ubiquitin and microtubule–associated protein tau immunoreactivity each define distinct structures with differing distributions and solubility properties in Alzheimer brain," *Proc. Natl. Acad. Sci. USA*, 85:2854–2858, 1988.

Shin et al., "Hydrated Autoclave Pretreatment Enhances TAU Immunoreactivity in Formalin–Fixed Normal and Alzheimer's Disease Brain Tissue," *Lab. Invest.*, 64:693–702, 1991.

Shin et al., "Increased Tau Accumulation in Senile Plaques as a Hallmark in Alzheimer's Disease," *Am. J. Pathol.*, 134:1365–1371, 1989.

Shin et al., "Alzheimer disease A68 proteins injected into rat brain induce codeposits of β–amyloid, ubiquitin, and α1–antichymotrypsin," *Proc. Natl. Acad. Sci. USA*, 90:6825–6828, 1993.

Smith et al., "Measurment of Protein Using Bicinchoninic Acid," *Anal. Biochem.*, 150:76–85, 1985.

Snow et al., "The Presence of Heparan Sulfate Proteoglycans in the Neuritic Plaques and Congophilic Angiopathy in Alzheimer's Disease," *Am. J. Pathol.*, 133:456–463, 1988.

Spillantini et al., "Topographical relationship between β–amyloid and tau protein epitopes in tangle–bearing cells in Alzheimer disease," *Proc. Natl. Acad. Sci. USA*, 87:3952–3956, 1990.

Springall et al., "The Potential of the immunogold–silver staining method for paraffin sections," *Histochem*, 81:603–608, 1984.

Tohyama et al., "Molecular Milestones That Signal Axonal Maturation and the Committment of Human Spinal Cord Precursor Cells to the Neuronal or Glial Phenotype in Development", *J. Comp. Neurol.* 3100: 285–299 (1991).

Trojanowski et al., "Altered Tau and Neurofilament Proteins in Neuro–Degenerative Diseases: Diagnostic Implications for Alzheimer's Disease and Lewy Body Dementias," *Brain Pathol.*, 3:45–54, 1993.

Trojanowski et al., "Distribution of Tau Proteins in the Normal Human Central and Peripheral Nervous System," *J. Histochem. Cytochem.*, 37:209–215, 1989.

Vallee, "A Taxol–dependent Procedure for the Isolation of Microtubules and Microtubule–associated Proteins (MAPs)," *J. Cell Biol.*, 92:435–442, 1982.

Wisniewski and Frangione, "Apolipoprotein E: A Pathological Chaperone Protein in Patients with Cerebral and Systemic Amyloid", *Neurosci. Lett.* 135: 235–238 (1992).

Wolozin et al., "A Neuronal Antigen in the Brains of Alzeheimer Patients," *Science*, 232:648–650, 1986.

Yamaguchi et al., "Secondary Desposition of Beta Amyloid within Extracellular Neurofibrillary Tangles in Alzheimer–type Dementia," *Am. J. Pathol.*, 138:699–705, 1991.

Bondareff et al., "Molecular Analysis of Neurofibrillary Degeneration in Alzheimer's Disease", *Am. J. of Pathology* 137: 711–723 (1990).

Kondo et al., "The Carboxyl Third of Tau is Tightly Bound to Paired Helical Filaments", *Neuron* 1: 827–834 (1988).

Okazaki et al., "Staurosporine, a Novel Protein Kinase Inhibitor, Enhances HL–60–Cell Differentiation Induced by Various Compounds", *Exp. Hematol.* 16: 42–48 (1988).

Seubert et al., "Isolation and Quantification of Soluble Alzheimer's β–Peptide From Biological Fluids", *Nature* 359: 325–327 (1992).

Shoji et al., "Production of the Alzheimer Amyloid β Protein by Normal Proteolytic Processing", *Science* 258: 126–129 (1992).

Wischik et al., "Isolation of a Fragment of Tau Derived from the Core of the Paired Helical Filament of Alzheimer Disease", *Proc. Natl. Acad. Sci. USA 85*: 4506–4510 (1988).

RAT COMPRISING STRAIGHT FILAMENTS IN ITS BRAIN

ACKNOWLEDGEMENT OF GOVERNMENT RIGHTS

This invention was made in the course of research sponsored by NIH grant number AG-09215. The Government has certain rights in this invention.

FIELD OF THE INVENTION

The present invention relates to non-human animal models, methods of generating non-human animal models, and compositions used in generating non-human animal models useful for studying human diseases, conditions, and disorders, especially those characterized by loss, damage, or dysfunction of the brain.

BACKGROUND OF THE INVENTION

The most prominent neuropathologic lesions that characterize the brains of individuals having Alzheimer's disease (AD) as well as elderly individuals with Down's syndrome include neurofibrillary tangles (NFTs), neuropil threads (NTs), and amyloid-rich senile plaques (SPs), which are associated with the massive loss of selected populations of central nervous system (CNS) neurons (Kosik, *Science,* 1992, 256, 780; Lee, et al., *Curr. Opin. Neurobiol.,* 1992, 2, 653; and Trojanowski, et al., *Brain Pathol.,* 1993, 3, 45). The NFTs associated with AD are composed principally of paired helical filaments (PHFs) which are biochemically and structurally distinct from the β-amyloid (Aβ) fibrils present in SP cores. Abnormally phosphorylated tau proteins, referred to as A68 or PHF-tau, are the building blocks of PHFs (Kosik, *Science,* 1992, 256, 780; Lee, et al., *Curr. Opin. Neurobiol.,* 1992, 2, 653; Goedert, et al., *Proc. Natl. Acad. Sci. USA,* 1993, 90, 5066; and Trojanowski, et al., *Brain Pathol.,* 1993, 3, 45). In contrast, the subunit proteins of Aβ fibrils are 39–43 amino acid long Aβ peptides derived from one or more larger, alternatively spliced amyloid precursor proteins (βAPPs) (Trojanowski, et al., *Brain Pathol.,* 1993, 3, 45; Hardy, *J. NIH Res.,* 1993, 5, 46; Mullan, et al., *Trends Neurosci.,* 1993, 16, 409; and Selkoe, *Trends Neurosci.,* 1993, 16, 403).

Although PHFs and Aβ fibrils are the most distinct structural elements in NFTs and SPs, respectively, a number of other components selectively accumulate in SPs and NFTs including ubiquitin (Mori, et al., *Science,* 1987, 235, 1641; Perry, et al., *Proc. Natl. Acad. Sci. USA,* 1987, 84, 3033; and Shaw, et al., *Proc. Natl. Acad. Sci. USA,* 1988, 85, 2854) and αl-antichymotrypsin (ACT) (Abraham, et al., *Cell,* 1987, 52, 487; and Gollin, et al., *NeuroReport,* 1992, 3, 201). Other components found in NFTs and SPs include heparan sulfate proteoglycans (HSPGs) (Snow, et al., *Am. J. Pathol.,* 1988, 133, 456; Perlmutter, et al., *J. Neurosci. Res.,* 1991, 30, 673; and Perry, et al., *J. Neurosci.,* 1991, 11, 3679) and apolipoprotein E (ApoE), a recently defined risk factor for sporadic and familial AD (Namba, et al., *Brain Res.,* 1991, 541, 163; Wisniewski, et al., *Neurosci. Lett.,* 1992, 135, 235; Saunders, et al., *Neurol.,* 1993, 43, 1467; and Schmechel, et al., *Proc. Natl. Acad. Sci. USA,* 1993, 90, 9649). In addition, aluminum has also been detected in NFTs and/or tangle-bearing neurons (Perl, et al., *Science,* 1980, 208, 297; Garruto, et al., *Proc. Natl. Acad. Sci. USA,* 1984, 81, 1875; Picardo, et al., *ACTA Neuropathol.,* 1988, 77, 1; and Good, et al., *Ann. Neurol.,* 1992, 31, 286) as well as in some SPs (Candy, et al., *Lancet,* 1986, i, 354; and Candy, et al., *J. Neurol. Sci.,* 1992, 107, 210).

It has been observed that SPs are sites at which abundant accumulations of both PHFs and Aβ fibrils converge in the same lesion (Trojanowski, et al., *Brain Pathol.,* 1993, 3, 45). PHFs are the building blocks of two types of dystrophic neurites, NTs and the smaller abnormal processes that surround the amyloid rich cores of SPs (Braak, et al., *Neurosci. Lett.,* 1986, 65, 35; and Kidd, *Brain,* 1964, 87, 307). It has been postulated that the release of A68 from degenerating neurons or their processes in the AD brain contributes to the formation of SPs by interacting with the Aβ that is normally secreted by neural cells (Shin, et al., *Proc. Natl. Acad. Sci. USA,* 1993, 90, 6825). The generation of the neuropathological lesions in the brain of an individual having AD invariably accompany the clinical dementia associated with AD. Thus, reproduction of these lesions, or deposition of compounds found therein, in the brain of a non-human animal would provide an animal model for AD. This non-human animal model would also provide for screening of putative therapeutic and prophylactic compositions.

The paucity of in vivo and in vitro model systems for studying AD, and in particular, the pathobiology of A68 and Aβ, has proven to be a major impediment to the development of an effective therapy for individuals suffering from AD and to providing prophylactic treatment for those individuals susceptible to AD. Currently, the only source of NFTs and SPs is human cadavers, which does not allow for adequate examination of the process of NFT and SP formation. Accordingly, mechanistic hypotheses that attempt to explain the accumulation of A68, Aβ, ACT, and ubiquitin in SPs and NFTs (Perry, et al., *Am. J. Pathol.,* 1992, 140, 283; Yamaguchi, et al., *Am. J. Pathol.,* 1991, 138, 699; Spillantini, et al., *Proc. Natl. Acad. Sci. USA,* 1990, 87, 3952; Arai, et al., *Proc. Natl. Acad. Sci. USA,* 1990, 87, 2249; Shin, et al., *Am. J. Pathol.,* 1989, 134, 1365; Mori, et al., *Science,* 1987, 235, 1641; Cole, et al., *Neurosci. Lett.,* 1987, 79, 207; Perry, et al., *Proc. Natl. Acad. Sci. USA,* 1987, 84, 3033; Abraham, et al., *Cell,* 1987, 52, 487; and Gollin, et al., *NeuroReport,* 1992, 3, 201), or the pathogenesis of SPs, NFTs, and other AD lesions are nearly impossible to validate solely by studying postmortem human brain tissue.

There is a need for animal models of CNS diseases and disorders such as animals which produce conditions which resemble or mimic the symptoms and pathology associated with CNS diseases, conditions, or disorders. There is a need for methods of generating animal models of CNS diseases and disorders such as animals which develop physical characteristics that model or mimic CNS diseases, conditions, or disorders. There is also a need for compositions useful to generate animal models of CNS diseases and disorders such as animals which develop physical characteristics that resemble or mimic CNS diseases, conditions, or disorders. There is also a need for a method of identifying compositions useful to treat individuals suspected of suffering from CNS diseases, conditions, or disorders. There is a need to develop a non-human animal model with which to investigate the development of AD neuropathological lesions and also provide a system with which to evaluate potential therapeutic and prophylactic compositions.

SUMMARY OF THE INVENTION

The present invention relates to a method of generating a non-human animal model, wherein the model animal contains Aβ deposits in its brain. An amount of human A68 protein sufficient to result in formation of the Aβ deposits is injected into the brain of the model animal.

The present invention also relates to a non-human animal model characterized by the presence of Aβ deposits in its brain. These Aβ deposits are formed by injecting an amount of human A68 protein, sufficient to result in formation of the Aβ deposits, into the brain of the model animal.

The present invention also relates to a non-human animal model characterized by the presence of Aβ deposits comprising human A68, Aβ, ubiquitin, and α1-antichymotrypsin, in its brain.

The present invention also relates to a composition comprising human A68, or a salt thereof, in a liquid vehicle suitable for injection.

The present invention also relates to a composition comprising human A68, or a salt thereof, in combination with a compound that comprises aluminum, in a liquid vehicle suitable for injection.

The present invention also relates to a method of evaluating putative therapeutic and prophylactic compositions. The model animal having Aβ deposits is treated with the putative therapeutic composition and is subsequently evaluated and compared to a control model animal which does not undergo the putative therapeutic regimen. Alternatively, the animal is treated with the putative prophylactic composition prior to generation of the Aβ deposits and is subsequently evaluated and compared to a control model animal which does not undergo the putative prophylactic regimen.

BRIEF DESCRIPTION OF THE DRAWINGS

FIG. 1(A–H) depicts photomicrographs of brain sections of rats injected with human A68 (panels A–D), human DEP-A68 (panels E–F), or normal adult human tau protein (panel G) sacrificed one hour (panels A, E and G), two days (panel B and F), one week (panel C), or four weeks (panel D) post-injection. The sections were probed with monoclonal antibody (Mab) T14. The arrows in panels F and H identify the injection site. Panels A, B, F and G were magnified 11×; panel C was magnified 53×; panel D was magnified 85×; and panel E was magnified 27×.

FIG. 2(A–G) depicts photomicrographs of brain sections of rats previously injected with human A68 and sacrificed two days post-injection. The sections were probed with T3P antibody (panel A), Alz50 antibody (panel B), anti-ubiquitin antibody before (panel C) and after (panel D) absorption with ubiquitin (Sigma Chemical Co., St. Louis, Mo.), UP107 antibody to Aβ before (panel E) and after (panel F) absorption with synthetic Aβ (amino acids 1–40), and anti-ACT antibody before (panel G) and after (panel H) absorption with recombinant human ACT. Panels A–H were magnified 32×.

FIG. 3(A–B) depicts immunoelectron photomicrographs of brain sections, specifically the A68 injection sites, of rats sacrificed one day post-injection. The brain sections were labeled with antisera to A68 (T3P antibody, panel A), or Aβ (1280 antibody, panel B), and silver intensified immunogold particles. The nucleus (N) of the intact cell in the lower right corner of panels A and B is identified. Panel A was magnified 26,700× and panel B was magnified 44,500×.

DETAILED DESCRIPTION OF THE PREFERRED EMBODIMENTS

As used herein, the term "neuropathological lesion" is meant to refer to NFTs, NTs, and SPs. Neurological lesions are neurological abnormalities present in individuals having CNS diseases, conditions, or disorders such as AD.

As used herein, the term "A68" and "PHF-tau" are used interchangeably and are meant to refer to abnormally phosphorylated tau protein. A68 is abnormally phosphorylated at Ser$^{396}$ of the tau protein, as well as at additional Ser and Thr residues followed by a Pro residue.

As used herein, the term "DEP-A68" is meant to refer to A68 protein which has been dephosphorylated.

As used herein, the term "Aβ deposit" is meant to refer to the neuropathological matter that is generated in the brain of the model animal subsequent to injection with a composition comprising human A68. The Aβ deposit may include other compounds such as A68, ubiquitin, ACT, ApoE, HSPG, aluminum, and other lesion-associated material that may be codeposited with A68 and Aβ. The Aβ deposit may appear as amorphous material in photomicrographs of brain sections, and also as amyloid fibrils.

Aβ deposits which develop in the brains of animals injected with A68 resemble those observed in human brains during the early stages of formation of neurological lesions in humans suffering from AD and other neurological amyloidoses. Thus, the initiation of Aβ deposit formation in animal models of the invention allows for the production of animal models useful to study the early stages of formation of neurological lesions and compounds and treatments which effect the early stages of formation of neurological lesions. Such animal models are therefore particularly useful in studying the progress of Aβ deposition and compounds and activities which modulate such progress.

One aspect of the present invention is a method of generating non-human animal models of progressive neurodegenerative disorders which affect humans. CNS diseases and disorders which may be modeled by practicing the methods of the present invention include any disease of the CNS which is characterized by NFTs or SPs, such as Alzheimer's disease, Parkinson's disease, Huntington's disease, amyotrophic lateral sclerosis, hereditary ataxia, motor neuron, and Lewy body disease. The present invention provides a non-human animal model of the initiation of Aβ deposition observed in a human disease, disorder, or condition. The present invention provides compositions for and methods of generating and using a non-human animal model of a human disease, disorder, or condition, especially those characterized by loss, damage, or dysfunction of the brain such as neurological disorders characterized by amyloidosis.

The present invention provides a non-human animal model in which Aβ and human A68 accumulate in Aβ deposits in the brain of the animal. Such an animal model provides a means to examine pathological conditions associated with early stages of AD. Such an animal model allows for examination of NFTs and SPs as well as the specific compounds which accumulate therein. In addition, such an animal model is useful in a method of screening and evaluating therapeutic and prophylactic compositions and treatments.

The present invention is particularly suited for examining AD, an amyloidosis, a condition in which certain proteins or protein fragments precipitate in various neurological tissues as amyloid, fibrillar aggregates. AD is also characterized by the presence of neuritic lesions and cell death. Heretofore, it has been difficult to physiologically examine the effectiveness of putative therapeutic or prophylactic compositions due to the absence of an appropriate animal model.

The animal model of the present invention may be generated by injecting a composition comprising human A68 into the brain of a non-human animal. Shortly after injection of A68, Aβ deposits are found in the brain which appear as aggregates of amorphous material. This amorphous material has been examined by a variety of immunohistochemical methods to determine the composition of the Aβ deposits. The Aβ deposits in the animal models according to the present invention have been observed to comprise human A68, Aβ, ACT, and ubiquitin. In contrast, injection of DEP-A68 or normal adult tau into the brain of a non-human animal produces no Aβ deposits.

Figure 1A:
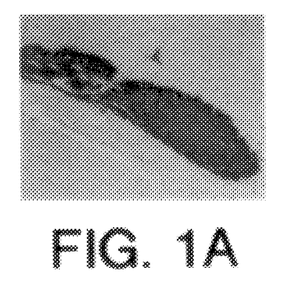
Figure 1B:
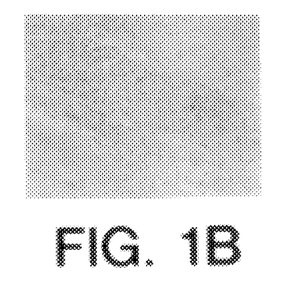
Figure 1C:
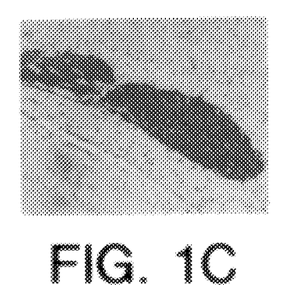
Figure 1D:
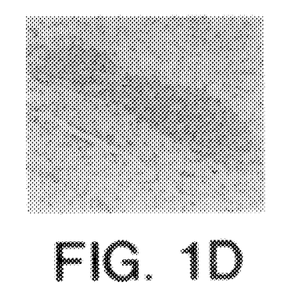
Figure 1E:
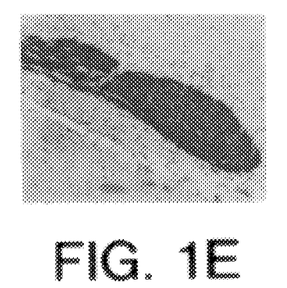
Figure 1F:
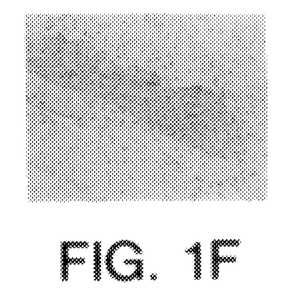
Figure 1G:
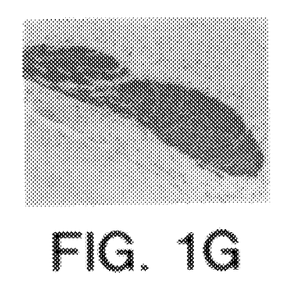
Figure 1H:
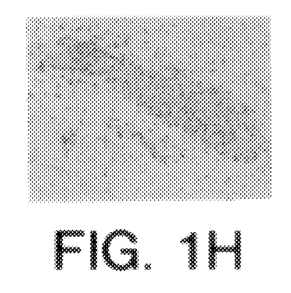
Figure 2A:
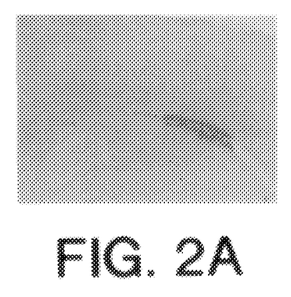
Figure 2B:
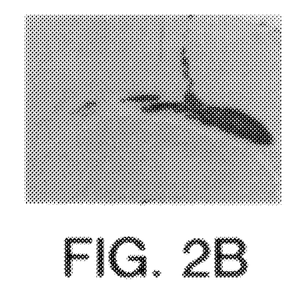
Figure 2C:
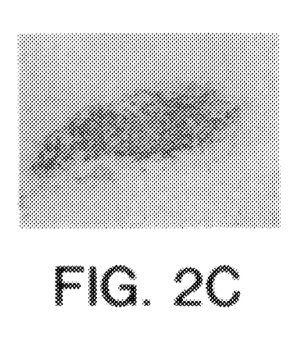
Figure 2D:
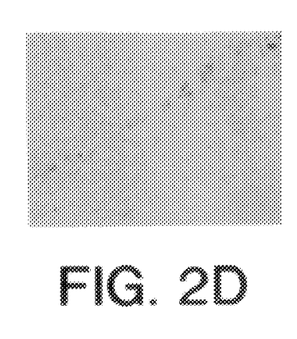
Figure 2E:
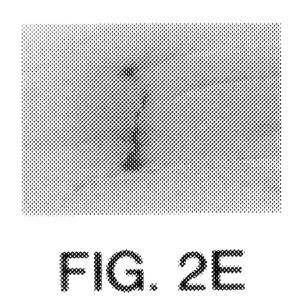
Figure 2F:
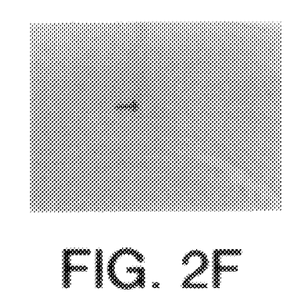
Figure 2G:
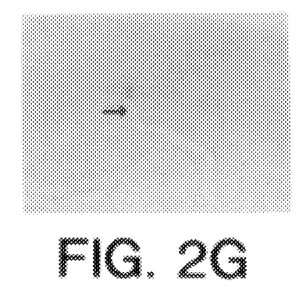
Figure 3A:
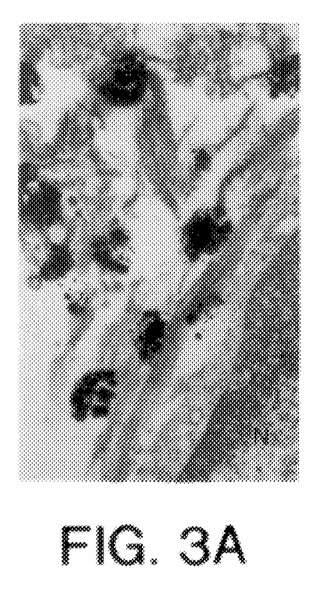
Figure 3B:
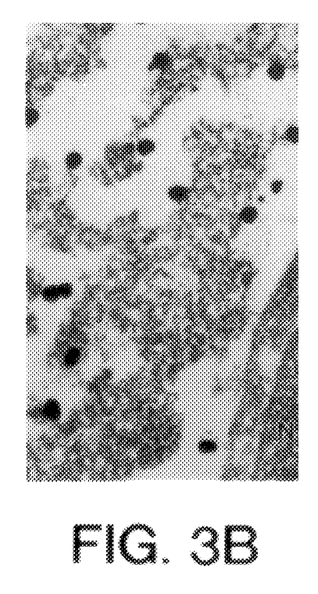

The Aβ deposits found in the brain of the animal after injection with A68 mimic the early stages of SP formation in the AD brain. Such Aβ deposits are depicted in FIGS. 1, 2, and 3. Thus, the present invention provides an animal model which mimics neuropathology found in the AD brain.

According to the present invention, a composition injected into the brain of the animal to generate the animal model comprises the human protein A68. According to some embodiments of the present invention, the composition comprising the human protein A68 is injected in conjunction with a compound or compounds which contain aluminum. According to some embodiments of the present invention, the composition that is injected into the brain of a non-human animal comprises a combination of human A68 protein and a compound or compounds that contain aluminum.

Injection of the compositions results in the formation of neuropathological matter that is similar to or mimics the pathology of a CNS disease or condition, such as Alzheimer's disease, particularly the early stages of amyloid deposition which lead to the development of amyloid plaques. The presence of A68 brings about changes in the animal's brain such that animal develops features which resemble or mimic the characteristics of the human CNS disease, condition, or disorder. The presence of aluminum together with A68 results in more profound development of these features and in the longer duration of time which they can be observed in the animal. Administration of A68 or, A68 in conjunction with aluminum, results in the formation of specific structures that, when present in the brain of the animal, give rise to conditions which resemble or mimic the pathology associated with the disease being modeled.

One preferred embodiment of the present invention provides a method of generating a non-human animal model that comprises Aβ deposits in its brain. The method comprises the step of administering or otherwise introducing into the brain of the animal, an amount of human A68, or a combination of human A68 and aluminum, sufficient to result in formation of the Aβ deposits.

The non-human animal of the present invention is preferably a mammal, more preferably a rodent. Preferred rodents are mice and rats. In preferred embodiments, the animal is a rat. However, any animal in which Aβ deposits may be formed as a result of injecting human A68 into the brain is included herein. While the strain of rat is not crucial to the effectiveness of the animal model, female Sprague/Dawley rats are a preferred strain of rats. Rats useful according to the invention preferably weigh about 170–280 g, although size is not a limiting factor. Rats can be of any age and may be obtained from any vendor or animal supplier known to those skilled in the art.

Human A68 protein is obtained post-mortem from humans having AD and is purified as described in Example 1. It is contemplated that human A68 may be produced synthetically in the laboratory by phosphorylation of tau. It is also contemplated that A68 from other animal species may be similarly produced. However, human A68 is preferred. It is intended that human A68 or fragments thereof may be used in the present invention. One skilled in the art would readily be able to generate fragments of A68 by a number of means and evaluate the ability of these fragments to generate the animal model set forth in the present invention.

In experiments using human DEP-A68 and/or normal adult tau as controls, human DEP-A68 may be obtained by dephosphorylating human A68 and normal adult tau protein is obtained post-mortem from individuals not having Alzheimer's disease.

According to some embodiments of the present invention, compounds which contain aluminum may be co-administered to animals in conjunction with A68 administration. In preferred embodiments, the compounds are administered as a single composition. In preferred embodiments, the aluminum is provided as a salt. In some preferred embodiments, the aluminum is provided as a salt selected from the group consisting of phosphate, sulphate, hydroxide, and the like. In preferred embodiments, the aluminum is provided as $AlCl_3$.

According to some preferred embodiments of the present invention, the non-human animal is first anesthetized, for example by intraperitoneal injections of Ketamine (87 mg/kg) and Xylazine (13 mg/kg), prepared for surgery and placed in a stereotaxic instrument (Kopf, Tujunga, Calif.). It should be noted that other methods and compositions for anesthetizing an animal may be employed as deemed appropriate by one skilled in the art.

A68 is preferably injected into the hippocampus, cerebrum, or medulla of the brain. A68 is most preferably injected into the cerebrum. However, it is anticipated that additional injection sites in the brain will suffice. The stereotaxic injection sites in each rat brain are determined using system B of Pellegrino et al.: -2.0 mm RC; 2.0 mm ML; 3.0 mm DV, -3.0 mm RC; 3.0 mm ML; 3.0 mm DV, and -4.0 mm RC; 4.0 mm ML; 4.0 mm DV (Pellegrino et al., in *A Stereotaxic Atlas Of The Rat Brain,* 1979, Plenum, N.Y., which is incorporated herein by reference). However, it is anticipated that other injection sites may also be appropriate as known to those skilled in the art. All injections should be performed over a short time period, such as 10 minutes, using a 10 μl Hamilton syringe or the like. After the injection, the needle should be left in place for about 10 minutes and then slowly removed. It is contemplated that a single injection or multiple injections in a single location or multiple locations may be performed, as decided by those skilled in the art.

Once the injection of A68 or, a combination of A68 and aluminum, is administered and has resulted in the formation of Aβ deposits, the animal may be sacrificed and the Aβ deposits can be examined. The formation of the Aβ deposits has been observed to occur as soon as one hour after injecting A68. However, the Aβ deposits may be observed until as late as 13 weeks post-injection. One skilled in the art will readily be able to adjust the time the animal is sacrificed depending upon the nature of the information sought. One skilled in the art will be familiar with the sacrificing of laboratory animals and the preparation of tissue within the sacrificed animal.

The tissue containing the Aβ deposits may be further analyzed for specific protein composition, including ubiquitin, α1-antichymotrypsin, as well as other proteins. Brain tissue is obtained, as described below, and examined by any number of means for the presence of Aβ deposits and deposit-forming compounds including A68, ubiquitin, α1-antichymotrypsin, Aβ, and aluminum. Such means may include morphological detection by light microscope, immunoelectron microscopy, Western blotting, SDS-PAGE, immunostaining, and other appropriate techniques known to those skilled in the art. These methods and others known to those skilled in the art may be used to determine the effectiveness of the injection, and thus for the generation of the animal model, and also for the evaluation of potential therapeutic and prophylactic compositions.

Another preferred aspect of the invention is a composition comprising A68 in an injectable form useful to generate non-human animal models. Human A68 is obtained post-mortem from brains of individuals suffering from AD and treated as described in Example 1. Compositions of human A68 may include acceptable liquid vehicles, such as saline, other buffers, or the like. The amount of A68 protein injected into the animal brain is preferably from about 10 ng to about 1 mg, more preferably from about 100 ng to about 100 $\mu$g, even more preferably from about 1 $\mu$g to about 10 $\mu$g and most preferably 3 $\mu$g. The volume of injection material is preferably about 1 $\mu$l to about 100 $\mu$l, more preferably about 3 $\mu$l. These volumes are not absolute and may be adjusted according to the animal being used. Thus, in some preferred embodiments, a composition comprising 10 ng–1 mg human A68 protein preferably in 1 $\mu$l–100 $\mu$l solution is provided. In some preferred embodiments, a composition comprising 100 ng–100 $\mu$g human A68 protein preferably in 1 $\mu$l–100 $\mu$l solution is provided. In some preferred embodiments, a composition comprising 1 $\mu$g–10 $\mu$g human A68 protein preferably in 1 $\mu$l–100 $\mu$l solution is provided. In some preferred embodiments, a composition comprising about 3 $\mu$g human A68 protein preferably in 3 $\mu$l solution is provided.

Another preferred aspect of the invention is an injectable combination of human A68 and aluminum. It is intended that any aluminum-containing composition may be used as the source of aluminum. Preferably an aluminum salt is used. Preferably, the aluminum salt is AlCl$_3$. One skilled in the art will readily be able to determine the concentration of the particular aluminum salt by standard techniques known to those skilled in the art. A 20 mM AlCl$_3$/0.5M Tris, pH 6.5 stock solution is preferably prepared and stored at 4° C. For co-injection with AlCl$_3$, A68 is mixed at 4° C. with a stock solution of AlCl$_3$, resulting in a final concentration of 10 mM AlCl$_3$/0.25M Tris pH 6.5, just prior to injection. The same amount of A68 injected alone is also used for co-injection with an aluminum salt. Preferably, the amount of AlCl$_3$ that is injected into the brain of an animal is 10 ng to 100 $\mu$g, more preferably 100 ng to 10 $\mu$g, most preferably at 4 $\mu$g. All freshly prepared solutions of A68 and aluminum should be injected within 2 hours after preparation. Thus, in some preferred embodiments, a composition comprising 10 ng–1 mg human A68 protein preferably in 1 $\mu$l–100 $\mu$l solution is provided. In some preferred embodiments, a composition comprising 100 ng–100 $\mu$g human A68 protein and 10 ng to 100 $\mu$g AlCl$^3$ preferably in 1 $\mu$l–100 $\mu$l solution is provided. In some preferred embodiments, a composition comprising 1 $\mu$g–10 $\mu$g human A68 protein and 100 ng to 10 $\mu$g AlCl$^3$ preferably in 1 $\mu$l–100 $\mu$l solution is provided. In some preferred embodiments, a composition comprising about 3 $\mu$g human A68 protein and about 4 $\mu$g AlCl$^3$ preferably in 3 $\mu$l solution is provided.

Another preferred aspect of the present invention is the identification of potential prophylactic or therapeutic compositions (test compounds) for the treatment of Alzheimer's disease pathology. The animal is treated with a range of concentrations of the test compound subsequent to (therapeutic) or prior to (prophylactic) establishment of the animal model with either A68 alone or A68 in combination with aluminum. The animal is treated immediately before (prophylactic) or after (therapeutic) injection of A68 or A68/aluminum, such as within an hour, or shortly thereafter, such as within days, as determined by those skilled in the art. The test compound may be administered intravenously, subcutaneously, or by whatever means is deemed appropriate by one skilled in the art depending upon the nature of the composition being tested. Controls are performed in which identical protocols are performed except for the absence of test compound. The animals are subsequently sacrificed and examined for the presence of A$\beta$ deposits as described previously. The period of time from treatment to sacrifice will vary from a matter of hours to weeks, as determined by those skilled in the art, depending upon the time course of therapeutic effectiveness for which one skilled in the art seeks results. The improvement or lack of improvement regarding the A$\beta$ deposits is then established by techniques described previously. An effective test compound inhibits, delays, or interferes with the formation of the A$\beta$ deposits in the animal brain compared to the control.

The present invention is further illustrated by the following examples, which are not intended to be limiting in any way.

EXAMPLES

Example 1
Generation of Non-Human Animal Model for Alzheimer's Disease
Method of isolating and human A68, dephosphorylated A68 and normal tau protein Human A68 was purified post-mortem from the brains of individuals suffering from Alzheimer's disease and/or individuals suffering from Down's syndrome and Alzheimer's disease (Lee, et al., *Science,* 1991, 251, 675; Bramblett, et al., *Lab. Invest.,* 1992, 66, 212; and Greenberg, et al., *Proc. Natl. Acad. Sci. USA,* 1990, 87, 5827). One skilled in the art will readily have access to post-mortem brains.

The isolation of A68 was performed on at least six different regions obtained in the same manner from fresh postmortem brain of each control and AD individual. These six regions follow: hippocampus, fornix, and frontal grey, frontal white, cerebellar grey matter, and cerebellar white matter. Of these six regions, PHF-rich neurofibrillary lesions (i.e., NFTs, SPs, and NTs) accumulate preferentially in the AD hippocampus and frontal grey matter but not in axon rich white matter (including the fornix) and cerebellum. Additionally, crude A68 was also isolated from several other cortical regions that develop variable numbers of NFTs, NTs, and SPs in AD (i.e., orbital, temporal, motor, parietal, and occipital).

Each tissue aliquot was meticulously dissected to remove extraneous components (e.g., leptomeninges and large blood vessels). Exactly 1 g samples of each region were obtained and then homogenized in a Potter-Elvehjem glass vessel with 1.1 ml of reassembly buffer (100 mM 2-[N-morpholino]-ethane sulfonic acid, 1 mM EGTA, 0.5 mM MgSO$_4$, 2 mM dithiothreitol, pH 6.8) supplemented with 0.5 mM phenylmethyl sulfonyl fluoride, and 1 $\mu$g/ml each of N-tosyl-lysine chloromethyl ketone, N-tosyl-L-phenylalanylchloro-methyl ketone, pepstatin A, leupeptin, and soybean trypsin inhibitor, to minimize proteolysis. The homogenates were centrifuged in an SS-34 rotor (Sorvall) at 11,000× g for 20 minutes and then in a Beckman TL45 rotor at 50,000× g for 60 minutes at 4° C. The resulting supernatants contained tau protein, whereas A68 remained in both cold pellets.

A68 was further isolated from the aforementioned cold pellets following the protocol of Ksiezak-Reding, et al., *J.*

Neurosci. Res., 1990, 25, 420, which is incorporated herein by reference. Briefly, the pellets obtained from the first and second cold centrifugation were combined and resuspended in 10 ml of A68 extraction buffer (10 mM Tris, 10% sucrose, 0.85M NaCl, 1 mM EGTA, pH 7.4) and centrifuged at 15,000× g for 20 minutes. The pellet was re-extracted in the same fashion, and the supernatants were pooled, made 1% in Sarkosyl, and incubated at room temperature for 30 minutes with gentle agitation. The solution was then centrifuged for 30 minutes in a Beckman 60 Ti rotor at 60,000×g.

After sarkosyl (N-lauroyl-N-methylglycine) extraction and centrifugation, pellets containing A68 were resuspended in buffer (0.1M MES, 0.17M NaCl, 1 mM $MgCl_2$, 1 mM EGTA, pH 7.0), boiled for 5 minutes and loaded onto a 1.0 to 2.5M sucrose gradient. Highly purified A68 proteins, which were completely solubilized in SDS sample buffer, were recovered between the 2.25 to 2.5M sucrose fractions and consisted of three to four polypeptides with an $M_r$ of 60 to 68 kDa. This protocol allowed the isolation of highly purified A68 consistently from NFT-rich cortex from patients with AD and from elderly individuals with Down's syndrome.

To render A68 water soluble for injection, A68 was further purified. After sucrose gradient centrifugation (Lee, et al., Science, 1991, 251, 675; and Bramblett, et al., Lab. Invest., 1992, 66, 212), the 1.25 to 2.0M and 2.25 to 2.5M sucrose fractions were extracted in 2M guanidine isothiocyanate at 37° C. for 60 minutes, and the guanidine-insoluble material was removed by further centrifugation for 30 minutes at 100,000×g. The supernatant was exhaustively dialyzed against distilled water, and the water insoluble material was removed by centrifugation once again. The resulting supernatant was lyophilized and used for injection into rats as well as for the generation of DEP-A68. This guanidine-extracted, water soluble supernatant was shown by Western blots to contain purified A68.

DEP-A68 was generated from A68 by enzymatic dephosphorylation following an overnight incubation in 20 U/ml of Type III-N E. coli alkaline phosphatase at 37° C. (Lee, et al., Science, 1991, 251, 675).

Normal adult human tau protein was prepared as described in Lee, et al., Science, 1991, 251, 675, and Bramblett, et al., Lab. Invest., 1992, 66, 212, which is a modification of a previously described procedure (Baudier, et al., J. Biol. Chem., 1987, 262, 17584). Briefly, 500–600 g samples of normal cerebral cortex were freed of meninges and blood vessels and homogenized in a Waring blender with an equal volume of reassembly buffer containing 0.75M NaCl, 0.5 mM PMSF, and 1 µg/ml each of N-tosyl-lysine chloromethyl ketone, N-tosyl-L-phenylalanylchloromethyl ketone, leupeptin, pepstatin A, and soybean trypsin inhibitor. This and all subsequent steps were performed at 4° C. unless otherwise stated. The homogenate was then centrifuged at 8000×g for 15 minutes and then at 65,000×g for 60 minutes. The supernatant was boiled and then made 50% saturated in ammonium sulfate and stirred overnight. The pelleted precipitate was resuspended in a minimum volume of water and dialyzed against half concentrated reassembly buffer. The precipitate was removed by centrifuging at 50,000×g for 20 minutes. Perchloric acid was added slowly to a final concentration of 2.5%, and the acid-insoluble contaminants were removed by centrifugation at 50,000×g for 30 minutes. The supernatant was again dialyzed against half concentrated reassembly buffer, and the protein concentration was determined using bicinchoninic acid with bovine serum albumin as a standard (Smith, et al., Anal. Biochem., 1985, 150, 76). A 10-fold amount of phosphocellulose tubulin (relative to tau) was added, and tau proteins were isolated further by taxol (Vallee, J. Cell Biol., 1982, 92, 435). Finally, tau-rich isolates were boiled and centrifuged to remove small amounts of contaminating tubulin, and the protein concentration was determined again using bicinchoninic acid as a dye reagent. By using this procedure, the typical yield of normal tau-proteins from 500–600 g of human cerebrum ranged from 10 to 14 mg. This procedure differed from previous methods reported by others, which generated pure tau from animal tissues (Grundke-Iqbal, et al., J. Biol. Chem., 1986, 261, 6084) in that purification steps (i.e., perchlorate or heat treatment and ammonium sulfate precipitation) were performed on an extract of cerebral cortex rather than cycled microtubule protein, which is difficult to obtain from human tissue due to the sensitivity of tubulin to post mortem interval.

Characterizing isolated human A68, dephosphorylated A68 and normal tau protein

Aliquots of the A68, DEP-A68 and normal adult human tau preparations that were used for injection were analyzed by gel electrophoresis and by Western blots using epitope specific antibodies to A68 and tau according to previously described methods in order to assess their purity (Lee, et al., Curr. Opin. Neurobiol., 1992, 2, 653; Trojanowski, et al., Brain Pathol., 1993, 3, 45; Lee, et al., Science, 1991, 251, 675; and Bramblett, et al., Lab. Invest., 1992, 66, 212). The anti-tau and anti-A68 antibodies included: Alz50, reactive to residues 2–10; T60, reactive to residues 119–150; T14, reactive to residues 141–178; T46, reactive to residues 404–441; Tau1, which recognized tau and DEP-A68, but not A68, and binds to a non-phosphorylated epitope within residues 189–207; T3P, which recognizes A68 but not tau or DEP-A68 and binds to an epitope within residues 389–402 that contains a phosphate at $Ser^{396}$; and PHF1, which is similar to the T3P antiserum (Lee, et al., Curr. Opin. Neurobiol., 1992, 2, 653; Trojanowski, et al., Brain Pathol., 1993, 3, 45; Lee, et al., Science, 1991, 251, 675; Bramblett, et al., Lab. Invest., 1992, 66, 212; Greenberg, et al., Proc. Natl. Acad. Sci. USA, 1990, 87, 5827; Greenberg, et al., J. Biol. Chem., 1992, 267, 564; Wolozin, et al., Science, 1986, 232, 648; Binder, et al., J. Cell Biol., 1985, 101, 1371; Papasozomenos, et al., Cell Motil. Cytoskeleton, 1987, 8, 210; and Lang, et al., Biochem. Biophys. Commun., 1992, 187, 783). The numbering system for the amino acids in tau protein referred to herein is based on the largest tau isoform as described in Goedert, et al., Neuron, 1992, 8, 159.

Method of injecting A68, DEP-A68 and tau protein into rat brain

Female Sprague/Dawley rats (170–280 g) were anesthetized by intraperitoneal injections of Ketamine (87 mg/kg) and Xylazine (13 mg/kg), prepared for surgery and placed in a stereotaxic instrument (Kopf, Tujunga, Calif.). Multiple A68 samples were injected into cerebral cortex and hippocampus at three separate sites on one side, while control rats received similar injections of DEP-A68 and normal adult human tau. The three stereotaxic injection sites in each rat brain were determined using system B of Pellegrino et al.: −2.0 mm RC; 2.0 mm ML; 3.0 mm DV, −3.0 mm RC; 3.0 mm ML; 3.0 mm DV, and −4.0 mm RC; 4.0 mm ML; 4.0 mm DV (Pellegrino, et al., in A Stereotaxic Atlas Of The Rat Brain, 1979, Plenum, N.Y.). All injections were performed over 10 minutes using a 10 µl Hamilton syringe. After the injection, the needle was left in place for another 10 minutes and then slowly removed. The concentration of A68, DEP-A68 and tau was estimated by protein assay and immunoblots and approximately similar amounts of each (i.e., 3 µg) were injected in 3 µl of phosphate buffered saline (PBS) at each site.

For injections of A68 in combination with an aluminum salt, 20 mM $AlCl_3$ in 0.5M Tris, pH 6.5 was made as a stock solution and stored at 4° C. 3 µg of A68 was mixed at 4° C. with the stock solution of $AlCl_3$, resulting in a final concentration of 10 mM $AlCl_3$/0.25M Tris, pH 6.5, just prior to injection.

Preparation of animals for analysis

Following different post-injection survival times, the rats were lethally anesthetized and sacrificed by perfusion with PBS. The brains were removed and fixed by overnight immersion in 70% ethanol and 150 mM NaCl (Shin, et al., Proc. Natl. Acad. Sci. USA, 1993, 90, 6825). The post-injection survival times for rats injected with A68, DEP-A68 or tau were:

A68, 1 hour (n=5), 2 days (n=5), 1 week (n=6), 4 weeks (n=5), 8 weeks (n=3) and 13 weeks (n=2); DEP-A68, 1 hour (n=4), 2 days (n=4) and 1 week (n=4); and normal adult tau, 1 hour (n=4), 2 days (n=3), 1 week (n=3), 4 weeks (n=3), 8 weeks (n=1) and 13 weeks (n=1).

Light and electron microscopic immunohistochemical analysis of rat brain tissue

The methods for tissue processing and light microscopic immunohistochemical analysis have been described (Arai, et al., *Proc. Natl. Acad. Sci. USA,* 1990, 87, 2249; Lee, et al., *Science,* 1991, 251, 675; Bramblett, et al., *Lab. Invest.,* 1992, 66, 212; and Arai, et al., *Ann. Neurol.,* 1991, 30, 686). Briefly, the ethanol fixed rat brains were embedded in paraffin according to previously described infiltration schedules (Trojanowski, et al., *J. Histochem. Cytochem.,* 1989, 37, 209), and serial 6 μm thick sections through the injection sites were prepared and examined by immunohistochemistry (Schmidt, et al., *Lab. Invest.,* 1991, 64, 352; Tohyama, et al., *J. Comp. Neurol.,* 1991, 310, 285; Bramblett, et al., *Lab. Invest.,* 1992, 66, 212; and Shin, et al., *Proc. Natl. Acad. Sci. USA,* 1993, 90, 6825).

The antibodies used for immunohistochemistry included those described above to tau and A68, as well as a MAb to ubiquitin (Mab1510, Sigma, St. Louis), 6 different MAbs and polyclonal antisera to Aβ (UP107, 2332, 1280, 2β4, AMY33, 10D5) and antibodies to non-Aβ domains in the βAPPs (LN21 and LN27, which bind to epitopes within the first 200 residues of the βAPPs; anti-C15, which binds to the last 15 residues in the βAPPs). The specificities of these antibodies have been described (Arai, et al., *Proc. Natl. Acad. Sci. USA,* 1990, 87, 2249; Lee, et al., *Science,* 1991, 251, 675; Arai, et al., *Ann. Neurol.,* 1991, 30, 686; Hyman, et al., *Neuropathol. Exp. Neurol.,* 1992, 51, 76; Joachim, et al., *Nature,* 1989, 341, 226; and Hill, et al., *J. Comp. Neurol.,* 1991, 309, 150). Finally, antibodies to ACT also were used (ICN, Irvine, Calif. and DaKO, Sweden). The absorption of the antibodies for control experiments was performed as described (Arai, et al., *Proc. Natl. Acad. Sci. USA,* 1990, 87, 2249; and Shin, et al., *Lab. Invest.,* 1991, 64, 693).

Immunoelectron microscopic studies were performed on sections through the injection sites using procedures similar to those reported elsewhere (Springall, et al., *Histochem,* 1984, 81, 603; Balin, et al., *Brain Res.,* 1991, 556, 181; Hill, et al., *J. Comp. Neurol.,* 1991, 109, 150; Lee, et al., *Science,* 1991, 251, 675; Lee, et al., *Exp. Neurol.,* 1993, 121, 93; and Shin, et al., *Proc. Natl. Acad. Sci. USA,* 1993, 90, 6825). The rats were perfused with buffer and the brains were removed immediately thereafter and small pieces of tissue from the injection sites were excised an immersion fixed in 1% glutaraldehyde/2% paraformaldehyde in phosphate buffer for four hours, embedded in paraffin and then sectioned as described above. Pre-embedding immunoelectron microscopy was performed with a Hitachi 600 electron microscope using the T3P and the anti-Aβ antisera with 5 nm gold particles (Amersham, Arlington Heights, Ill.) and silver intensification as described (Lee, et al., *Science,* 1991, 251, 675; Hill, et al., *J. Comp. Neurol.,* 1991, 309, 150; Balin, et al., *Brain Res.,* 1991, 556, 181; and Springall, et al., *Histochem.,* 1984, 81, 603). Formic acid pre-treatment was used to enhance the Aβ immunoreactivity (Arai, et al., *Proc. Natl. Acad. Sci. USA,* 1990, 87, 2249; and Kitamoto, et al., *Lab. Invest.,* 1987, 57, 230).

Example 2

Analysis of Injected Rats

Aliquots of each of the A68, DEP-A68 and normal tau protein samples obtained as described previously were injected into rat brains and near serial sections of these brains (extending over the entire extent of the three injection sites) were examined by immunohistochemistry with the same anti-tau antibodies described previously. At 1 hour and 2 days after the injections of A68, aggregates of amorphous material were observed (FIG. 1, panels A and B), and they gradually disappeared from 1 to 13 weeks post-injection as macrophages and reactive astrocytes accumulated in the injection sites (FIG. 1, panels C and D). In contrast, DEP-A68 (FIG. 1, panels E and F) and normal human tau (FIG. 1, panel G) were eliminated from the injection sites within 2 days.

Specific domains in A68 were eliminated from the injection sites in a distinct temporal sequence as defined using epitope specific antibodies. The tau epitope containing phosphorylated $Ser^{396}$ (i.e., the epitopes recognized by PHF1 and T3P) persisted the longest in rat brain, whereas amino terminal tau epitopes (recognized by Alz50 (FIG. 2, panel B) and T60) were eliminated completely at 1 hour and 2 days post-injection, respectively, even though the Alz50 and T60 epitopes were present in A68 prior to injection. Tau epitopes located downstream of the Alz50 and T60 sites (recognized by T14, Tau1, T46 and Tau2) were extinguished more gradually, but none survived as long as the tau domain containing the phosphorylated $Ser^{396}$ site. Tau1 stained the A68 aggregates only after the sections were enzymatically dephosphorylated 15 indicating that rat brain phosphatases do not dephosphorylate A68.

Example 3

Analysis of the Interaction of A68 with Additional Proteins

To determine if injected A68 interacted with other proteins known to co-localize with A68 in NFTs and/or neuritic SPs in the AD brain (Perry, et al., *Am. J. Pathol.,* 1992, 140, 283; Yamaguchi, et al., *Am. J. Pathol.,* 1991, 138, 699; Spillantini, et al., *Proc. Natl. Acad. Sci. USA,* 1990, 87, 3952; Arai, et al., *Proc. Natl. Acad. Sci. USA,* 1990, 87, 2249; Shin, et al., *Am. J. Pathol.,* 1989, 134, 1365; Mori, et al., *Science,* 1987, 235, 1641; Cole, et al., *Neurosci. Lett.,* 1987, 79, 207; Perry, et al., *Proc. Natl. Acad. Sci. USA,* 1987, 84, 3033; Abraham, et al., *Cell,* 1987, 52, 487; and Gollin, et al., *NeuroReport,* 1992, 3, 201), adjacent sections from the same brains were probed using antibodies to ubiquitin, Aβ, and ACT. At 1 hour post-injection, weak or no ubiquitin and ACT staining in the A68 aggregates was noted, while intensely immunoreactive Aβ was present throughout the aggregates. Immunoreactivity for these same proteins was seen consistently throughout the A68 aggregates in all 5 rats sacrificed at 2 days post-injection (FIG. 2, panels C, E and G) and the immunoreactivity for these proteins was removed by absorbing the antibodies with the corresponding antigen (FIG. 2, panels D, F and H, respectively). These findings do not reflect contaminants in the A68 preparations since no ubiquitin, Aβ, or ACT immunoreactivity was detected in aliquots of A68 analyzed by 5 Western blots or by ELISA with the same antibodies used in the immunohistochemical studies. No deposition of Aβ, ubiquitin, or ACT immunoreactivity was observed in rat brains injected with DEP-A68 or normal adult tau, except for Aβ with DEP-A68 only at 1 hour post-injection. Further, human high molecular weight neurofilament subunits and fetal tau also were injected into rat brains as additional controls, but the results of these experiments were identical to those seen with normal adult tau.

Ubiquitin, Aβ, and ACT immunoreactivity co-localized with A68 as long as the A68 remained in the brain (i.e., for 4 weeks). Aβ and ACT immunoreactivity was more intense and abundant than the A68 and ubiquitin immunoreactivity at 1–4 weeks, and immunoreactive Aβ and ACT remained at the injection site for up to 13 weeks post-injection. In contrast to the anti-Aβ antibodies, none of the antibodies specific for amino and carboxy terminal epitopes in the βAPPs stained the A68 aggregates, and none of the aggregates were Congo red or Thioflavin S positive.

Example 4
Analysis of Rat Brain Tissue by Immunoelectron Microscopy

Immunoelectron microscopy performed on cortical injection sites containing A68 showed extracellular amorphous material and tightly bundled 10–25 nm straight filaments. The amorphous material was immunoreactive with both the T3P and the anti-Aβ antisera (FIG. 3, panels A and B), while the filaments were immunoreactive with the T3P antiserum (FIG. 3, panel A). Thus, at least some of the guanidine extracted A68 proteins reassembled into filaments similar to the straight filaments found associated with PHFs in NFTs and dystrophic neurites (Kosik, *Science,* 1992, 256, 780; Lee, et al., *Curr. Opin. Neurobiol.,* 1992, 2, 653; and Trojanowski, et al., *Brain Pathol.,* 1993, 3, 45).

Example 5
Screening Putative Therapeutic and Prophylactic Compositions

To screen potential therapeutic compositions for the treatment of AD pathology, the model animal is treated with a range of concentrations of the potential therapeutic composition subsequent to injection of the model animal with either A68 alone or in combination with an aluminum salt. To screen potential prophylactic compositions for the prevention of AD pathology, the model animal is treated with a range of concentrations of the potential prophylactic composition prior to the injection model animal with either A68 alone or in combination with an aluminum salt. To determine an effective therapeutic or prophylactic concentration, a range of concentrations should be administered to the animal in a series of tests.

The potential therapeutic or prophylactic composition may be administered intravenously, subcutaneously, or by whatever means is deemed appropriate by one skilled in the art depending upon the nature of the composition being tested. The animal is subsequently sacrificed and examined for the presence of Aβ deposits as described previously.

The animal is then compared to an untreated animal, which has previously received A68 injections without the putative therapeutic or prophylactic composition, and thus, has formed Aβ deposits. The improvement or lack of improvement regarding the Aβ deposits is then established by techniques described previously. The improvement or lack of improvement regarding the quantity, composition and size of the Aβ deposits may be established by techniques described above. An effective therapeutic or prophylactic composition may inhibit, delay, or interfere with the formation of the Aβ deposits in the animal brain.

What is claimed is:

1. A rat comprising straight filaments in its brain, wherein the rat is produced by injecting a sufficient amount of A68 protein to induce formation of said straight filaments.

2. The rat model of claim 1 wherein said human A68 protein is injected into said rat's brain in conjunction with aluminum.

3. The rat model of claim 1 wherein said human A68 protein is injected into said rat's brain as a composition comprising aluminum.

4. The rat model of claim 3 wherein said aluminum is injected as an aluminum salt.

5. The rat model of claim 4 wherein said aluminum salt is $AlCl_3$.

6. The rat model of claim 5 wherein said amount of $AlCl_3$ is from about 10 ng to about 100 μg.

7. The rat model of claim 1 wherein said human A68 protein is injected into the hippocampus of said brain.

8. The rat model of claim 1 wherein said human A68 protein is injected into the cerebrum of said brain.

9. The rat model of claim 1 wherein said amount of human A68 protein is from about 10 ng to about 1 mg.

10. A method of generating a rat comprising straight filaments in its brain comprising injecting into said rat's brain an amount of purified human A68 protein sufficient to induce the formation of said straight filaments.

11. The method of claim 10 wherein said human A68 protein is injected into the hippocampus of said brain.

12. The method of claim 10 wherein said human A68 protein is injected into the cerebrum of said brain.

13. The method of claim 10 wherein said amount of human A68 protein is from about 10 ng to about 1 mg.

14. The method of claim 10 wherein said amount of human A68 protein is from about 100 ng to about 100 μg.

15. The method of claim 10 wherein said amount of human A68 protein is from about 1 μg to about 10 μg.

16. The method of claim 10 wherein said amount of human A68 protein is 3 μg.

17. The method of claim 10 wherein said human A68 protein is injected into said rats brain in conjunction with aluminum.

18. The method of claim 17 wherein said human A68 protein is injected into said rat's brain as a composition comprising aluminum.

19. The method of claim 17 wherein said aluminum is injected as an aluminum salt.

20. The method of claim 19 wherein said aluminum salt is selected from the group consisting of aluminum phosphate, aluminum sulphate, aluminum hydroxide, and like aluminum salts.

21. The method of claim 19 wherein said aluminum salt is $AlCl_3$.

22. The method of claim 21 wherein said amount of $AlCl_3$ is from about 10 ng to about 100 μg.

23. The method of claim 21, wherein said amount of $AlCl_3$ is from about 100 ng to about 10 μg.

24. The method of claim 21, wherein said amount of $AlCl_3$ is 4 μg.

25. A method of identifying compositions which inhibit the formation of straight filaments in the brain comprising, a) administering a test composition to a rat, wherein the rat which has had injected into its brain a sufficient amount of purified human A68 protein to cause the formation of said straight filaments, and wherein the compound is administered to said rat prior to the formation said straight filaments;

b) comparing the brain of the rat in step a) with the brain of a rat which has had injected into its brain a sufficient amount of purified human A68 protein to cause the formation of said straight filaments, and wherein said rat did not receive the test composition; and c) evaluating said rats for the prophylactic effect of said test composition on the formation of said straight filaments.

26. A composition comprising human A68, or salt thereof, aluminum, and a liquid vehicle suitable for injection.

27. The composition of claim 26 wherein said aluminum is in the form of an aluminum salt.

28. The composition of claim 27 wherein said aluminum salt is $AlCl_3$.

* * * * *

UNITED STATES PATENT AND TRADEMARK OFFICE
CERTIFICATE OF CORRECTION

PATENT NO. : 5,849,988
DATED : December 15, 1998
INVENTOR(S) : Trojanowski et al.

It is certified that error appears in the above-identified patent and that said Letters Patent is hereby corrected as shown below: On the title page, Item [57], In the Abstract:
Delete Abstract in its entirety and Add --A method of generating a rat having straight filaments in its brain by injecting into the brain of the rat an amount of human A68 protein sufficient to result in the formation of the straight filaments. Rats are disclosed as having straight filaments similar to Alzheimer's Disease patients where the filaments are found associated with paired helical filaments and neurofibrillary tangles. Methods of screening test compositions for prophylactic activity by treating the A68 injected rats with the test compositions and evaluating the brains of the rats for straight filament formation.--

At col. 12, line 29, delete the number "15" between dephosphorylated" and indicating,
At col. 12, line 56, delete the number "5" between by and Western,
In claim 2 (col. 13, line 58) delete the word "model",
In claim 3 (col. 13, line 61) delete the word "model",
In claim 4 (col. 13, line 64) delete the word "model",
In claim 5 (col. 13, line 66) delete the word "model",
In claim 6 (col. 14, line 1) delete the word "model",
In claim 7 (col. 14, line 3) delete the word "model",
In claim 8 (col. 14, line 5) delete the word "model",
In claim 9 (col. 14, line 7) delete the word "model",
In claim 17 (col. 14, line 26) delete the word "rats" and insert --rat's--.

Signed and Sealed this

Twenty-fifth Day of May, 1999

Attest:

Q. TODD DICKINSON

*Attesting Officer*    *Acting Commissioner of Patents and Trademarks*